United States Patent
Storz et al.

(10) Patent No.: US 10,368,888 B2
(45) Date of Patent: Aug. 6, 2019

(54) MICROSURGICAL HOLDING AND/OR CUTTING INSTRUMENT

(71) Applicant: Aesculap AG, Tuttlingen (DE)

(72) Inventors: Stefan Storz, Tuttlingen (DE); Tom Schweitzer, Tuttlingen (DE)

(73) Assignee: Aesculap AG (DE)

(*) Notice: Subject to any disclaimer, the term of this patent is extended or adjusted under 35 U.S.C. 154(b) by 159 days.

(21) Appl. No.: 15/697,971

(22) Filed: Sep. 7, 2017

(65) Prior Publication Data
US 2017/0367721 A1    Dec. 28, 2017

Related U.S. Application Data

(62) Division of application No. 15/121,265, filed as application No. PCT/EP2015/053731 on Feb. 23, 2015, now Pat. No. 9,888,934.

(30) Foreign Application Priority Data

Feb. 27, 2014  (DE) .................. 10 2014 102 606

(51) Int. Cl.
*A61B 17/29* (2006.01)
*A61B 17/28* (2006.01)
(Continued)

(52) U.S. Cl.
CPC .............. *A61B 17/29* (2013.01); *A61B 17/28* (2013.01); *A61B 17/30* (2013.01);
(Continued)

(58) Field of Classification Search
CPC . A61B 17/28; A61B 17/2804; A61B 17/2816; A61B 17/29; A61B 17/30;
(Continued)

(56) References Cited

U.S. PATENT DOCUMENTS

| | | |
|---|---|---|
| 4,397,312 A | 8/1983 | Molko |
| 4,478,221 A | 10/1984 | Heiss |

(Continued)

FOREIGN PATENT DOCUMENTS

| | | | |
|---|---|---|---|
| CN | 102686172 A | 9/2012 | |
| DE | 144979 | * 10/1902 | ............. A61B 17/30 |

(Continued)

OTHER PUBLICATIONS

Chinese Office Action for Chinese Application No. 201580010968.5, dated May 17, 2018, with translation, 19 pages.

(Continued)

*Primary Examiner* — Diane D Yabut
*Assistant Examiner* — Socrates L Boutsikaris
(74) *Attorney, Agent, or Firm* — RatnerPrestia

(57) ABSTRACT

A surgical instrument includes a first lever element and a second lever element interconnected by a lever element hinge. Each lever element includes a grip portion and a jaw portion. A first spring portion and a second spring portion are proximally connected to the grip portions. A proximal free end of the first spring portion is coupled to a proximal free end of the second spring portion by a hinged joint. The hinged joint includes a hinge pin and at least one bearing eye. The at least one bearing eye forms a continuous longitudinal slit for radial insertion of the hinge pin. The slit extends diagonally relative to the axis of the at least one bearing eye so that at least one spring portion has to be twisted during radial insertion of the hinge pin into the at least one bearing eye.

10 Claims, 5 Drawing Sheets

Figure 3:
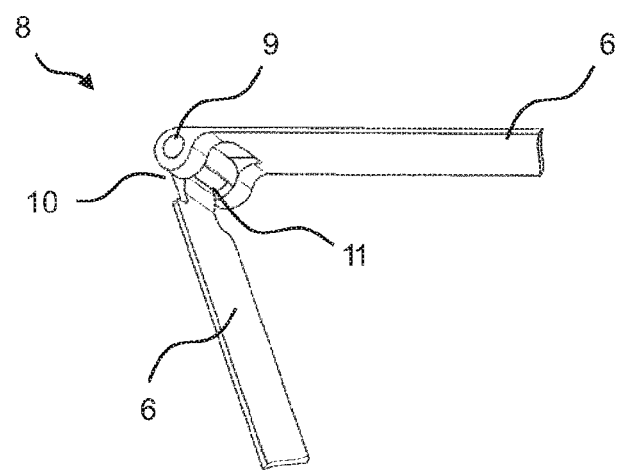

(51) Int. Cl.
*A61B 17/30* (2006.01)
*A61B 17/3201* (2006.01)
*A61B 90/00* (2016.01)
*A61B 17/00* (2006.01)

(52) U.S. Cl.
CPC ...... *A61B 17/3201* (2013.01); *A61B 17/2804* (2013.01); *A61B 17/2816* (2013.01); *A61B 2017/00429* (2013.01); *A61B 2017/00862* (2013.01); *A61B 2017/2845* (2013.01); *A61B 2017/2946* (2013.01); *A61B 2017/305* (2013.01); *A61B 2090/0813* (2016.02)

(58) Field of Classification Search
CPC ...... A61B 17/3201; A61B 2017/00429; A61B 2017/00862; A61B 2017/2845; A61B 2017/2946; A61B 2017/305; A61B 2090/0813
USPC .......................... 294/99.2; 606/174, 210–211
See application file for complete search history.

(56) References Cited

U.S. PATENT DOCUMENTS

| | | | |
|---|---|---|---|
| 5,065,516 A * | 11/1991 | Dulebohn | A61B 17/3201 30/245 |
| 5,269,790 A | 12/1993 | Funatsu | |
| 5,658,297 A | 8/1997 | Crainich | |

| | | | |
|---|---|---|---|
| 2010/0318102 A1 | 12/2010 | Cheng | |
| 2012/0016401 A1 | 1/2012 | Faulhaber et al. | |
| 2012/0303049 A1 | 11/2012 | Nakamura | |

FOREIGN PATENT DOCUMENTS

| | | |
|---|---|---|
| DE | 144979 C | 10/1903 |
| DE | 661032 C | 6/1938 |
| DE | 2919271 A1 | 11/1980 |
| DE | 3126578 A1 | 1/1983 |
| DE | 4115937 A1 | 5/1992 |
| EP | 2537476 A1 | 12/2012 |

OTHER PUBLICATIONS

International Search Report and Written Opinion of the International Searching Authority for International Application No. PCT/EP2015/053731 dated May 22, 2015, 9 pages.
German Search Report for German Application No. 10 2014 102 606.3 dated Dec. 16, 2014, including English translation, 10 pages.
Notice of Allowance for Application No. 15/121,265, dated Jun. 9, 2017, 9 pages.
Non Final Office Action for Application No. 15/121,265, dated Feb. 22, 2017, 24 pages.
Entire patent prosecution history of U.S. Appl. No. 15/121,265, filed Aug. 24, 2016, entitled, "Microsurgical Holding and/or Cutting Instrument".
Notice of Allowance for U.S. Appl. No. 15/121,265, dated Oct. 4, 2017, 11 pages.

* cited by examiner

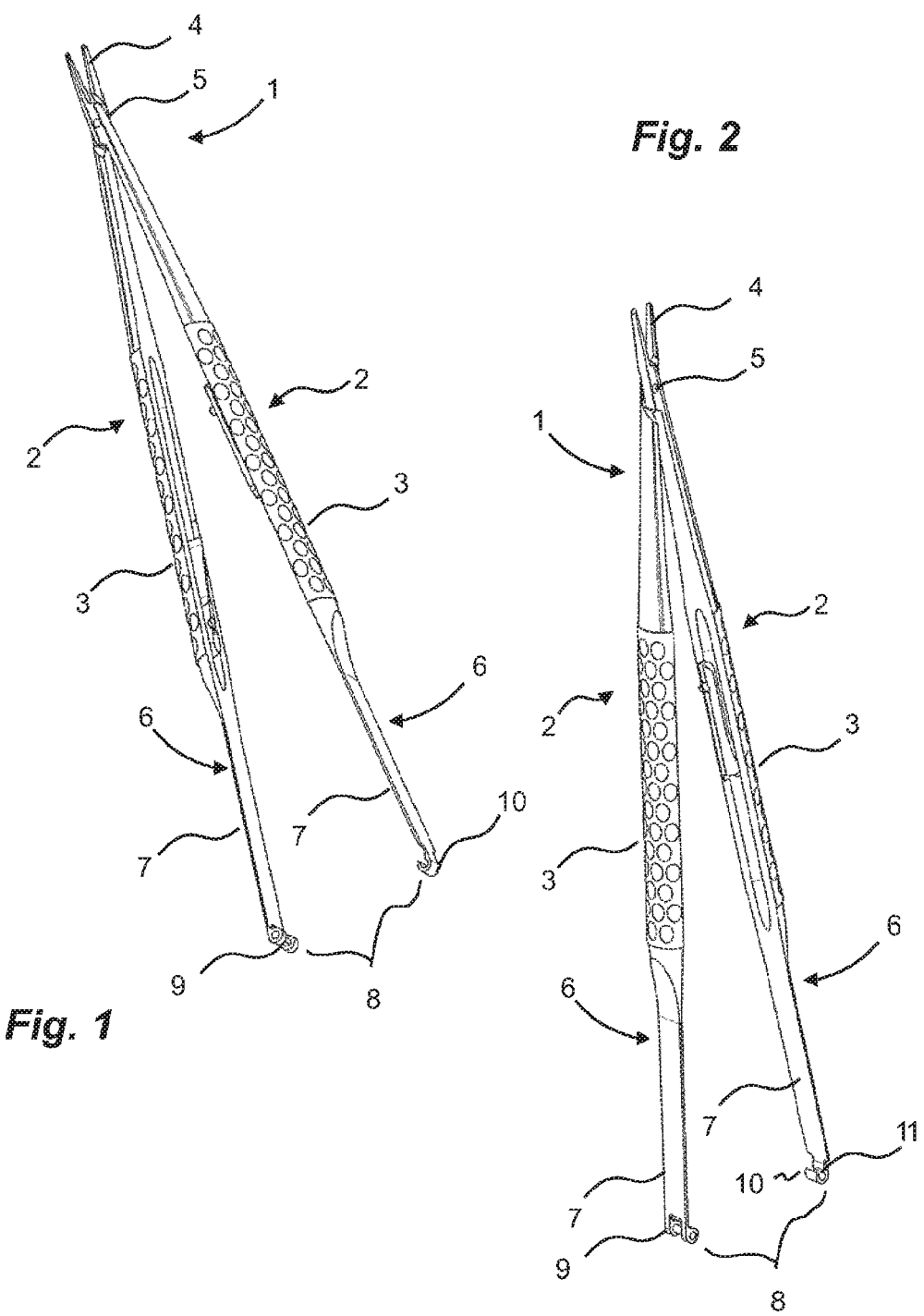

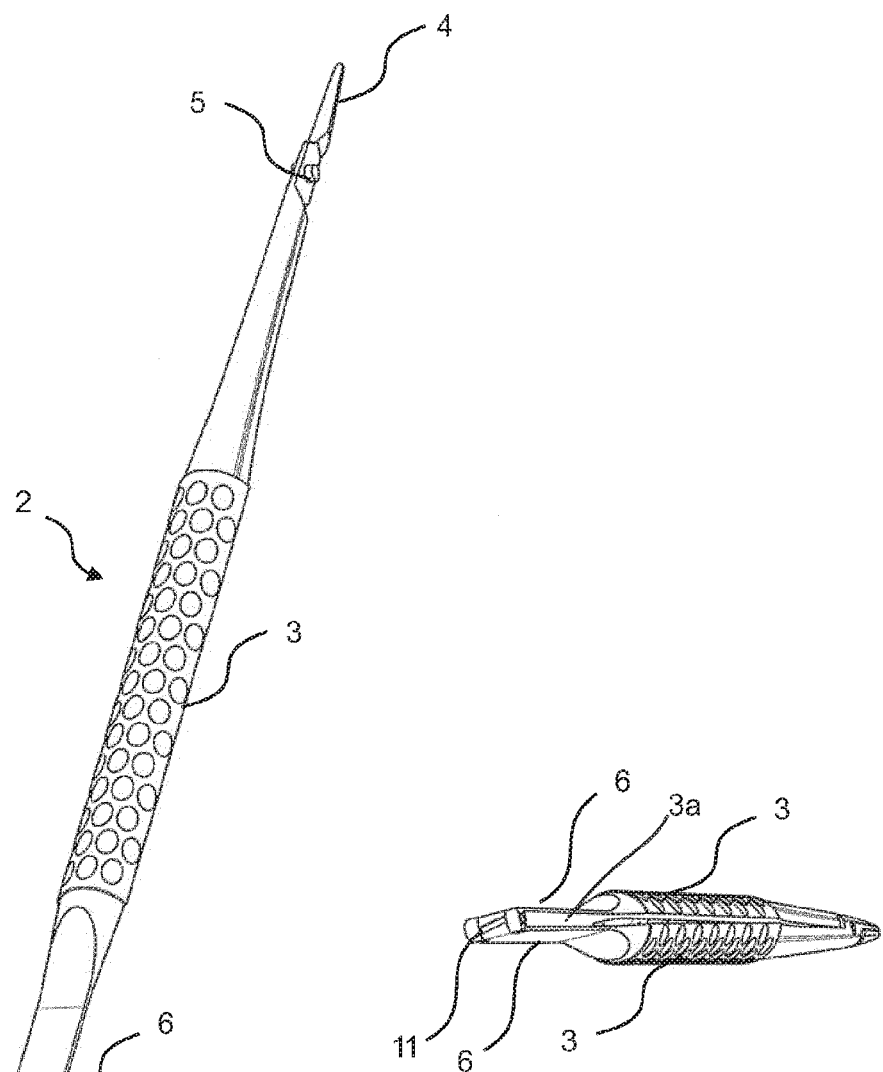
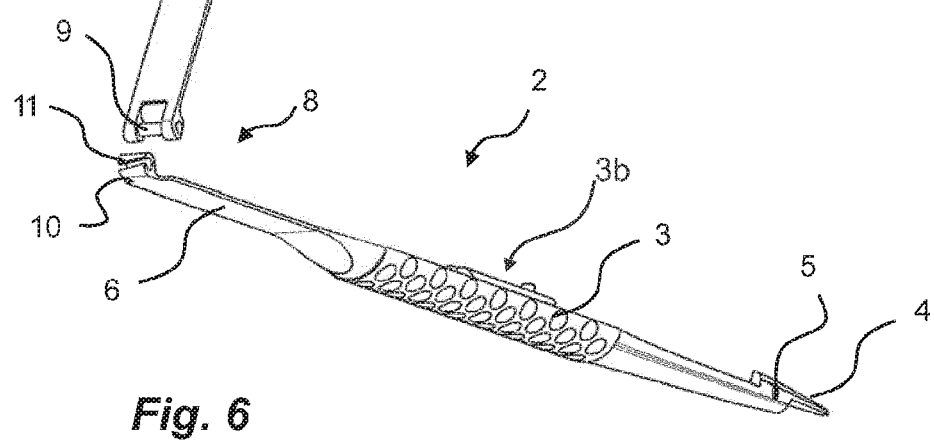
*Fig. 7*
*Fig. 6*

MICROSURGICAL HOLDING AND/OR CUTTING INSTRUMENT

RELATED APPLICATION(S)

This application is a divisional under 35 U.S.C. § 120 of U.S. application Ser. No. 15/121,265, filed Aug. 24, 2016, which is the United States national phase of International Application No. PCT/EP2015/053731, filed Feb. 23, 2015, which is related to and claims the benefit of priority of German Application No. DE 10 2014 102 606.3, filed Feb. 27, 2014. The contents of U.S. application Ser. No. 15/121, 265, International Application No. PCT/EP2015/053731 and German Application No. DE 10 2014 102 606.3 are incorporated by reference herein in their entireties.

FIELD

The invention relates to a micro surgical branch instrument, preferably a handheld instrument, for grasping, holding and/or cutting, for example, thin objects (needles, threads, wires etc.) or body tissue. Especially, but not exclusively, the invention relates to a surgical handheld instrument of the tongs and/or scissors type.

BACKGROUND

Micro surgical examinations and operations require handheld instruments which enable objects or body tissue in a patient to be grasped, held and cut, where necessary. For actuating the handheld instruments lever-type handles or grip shells are provided which are hinged to each other about a joint pivot bolt and are manually pivoting against each other for actuating instrument branches coupled thereto. If the manual actuating force on the handles/grip shells is dropped, the latter have to be forced apart again so as to return the instrument branches into their home positions. This is achieved, for example, by appropriate tensioning devices within the instrument such as resiliently flexible leaf springs. Said leaf springs may be mounted, for example, as external elements between the handles on the same or may be arranged as a proximal extension of the instrument at the proximal ends of the handles preferably integrally with the latter. Irrespective of the respective arrangement of the tensioning device, usually they have in common that the free ends of the leaf springs arranged at each of the two handles are coupled to each other, thus forming a kind of in-line connection of two leaf springs.

In order to be able to move the surgical instrument inter alia into a cleaning position, in surgical handheld instruments of this species, in particular in micro-scissors, microtongs and micro needle-holders, the free spring ends are juxtaposed in a state released from each other so as to be able to open the surgical handheld instrument completely via the pivot or hinge pin. For a detachable coupling/connection of the free leaf spring ends, manual micro-instruments established on the market make use of so called through-connections. In several through-connections of this type a T-shaped tab provided at the free end of the one leaf spring is pushed through a rectangular opening at the free end of the other leaf spring by twisting the two spring ends. Although the spring ends are positively coupled via the T-shaped tab, a form closure having large play is formed, however, so that the spring ends are not correctly guided during the operating movement of the two handles. In so far the leaf springs as well as the handles are guided exclusively on the pivot pin which, accordingly, should be press-fitted into pivot bores at the shell-type handles without large play.

For example, from the state of the art microsurgical forceps are known as described in DE 29 19 271 C2. Hence DE 29 19 271 C2 discloses a manual forceps instrument consisting of two grip plates or grip shells connected to a proximal (not releasable) joint via flat spiral or leaf springs, said grip plates or shells including a forceps-type, scissors-type or other gripping or holding branch at their respective distal ends. The springs are mounted to be exchangeable on the grip shells or grip plates, respectively. The proximal joint in this case is formed by a hinge pin pressed with eyelets formed at the flat spiral springs.

The previously known solutions suffer from the following drawbacks, however:

- Cleaning and conditioning of the surgical handheld instruments is difficult when the connection of the two leaf springs is not releasable, as the handles cannot be swiveled over any distance so as to reach as little overlapping of the handles and the instrument branches as possible in the area of the pivot bolt.
- Through-connections according to the known principle of the T-shaped tab and a rectangular opening are comparatively easy to uncouple, but usually they have considerable play. Therefore, they are completely unsuited for guiding the free ends of the leaf springs and thus indirectly for guiding the handles.
- A surgical glove may additionally be slightly clamped and thus damaged when handling a through-connection. This risk is given even in the case of surgical actuation of the instrument.
- By strongly twisting the spring ends when inserting the T-shaped tab into the rectangular opening, the material may be stressed by torsion which may possibly cause plastic deformation of the leaf springs. This may entail the fact that the two handles are no longer swiveled exactly in parallel to each other and thus get jammed.

SUMMARY

In view of the afore-explained problems, the invention is based on the object of creating an easily manageable, elegant and releasable connection for leaf spring ends on surgical handheld instruments of the afore-mentioned species. It is a preferred target to design the releasable connection so that it is comparatively easy to couple and to uncouple. It is another preferred target to design the releasable connection so that it is capable of adopting a guiding function at least for the leaf springs.

In order to achieve the given object as well as, where appropriate, to reach the preferred targets, a surgical handheld instrument of the forceps or scissors type is suggested.

The invention is based on the following idea:

The lever-type handles hinged to each other of a common (micro) surgical handheld instrument of the tongs or scissors type (not of the forceps type) are biased against each other by two leaf springs (proximally) arranged thereon whose respective free ends are releasably coupled to each other in a hinge-type manner. Preferably, each of the leaf springs is mounted or shaped in extension of a pertinent one of the lever-type instrument handles (grip shell) in the proximal direction and more preferably integrally with the respective pertinent instrument handle (handle lever). The two leaf springs (proximal spring portions of the two handles) exhibit a (preformed) curved shape (toward each other) at least in the initial position and preferably when the spring ends are not coupled so as to bring/hold/bias the two handles of the surgical handheld instrument against each other into the instrument opening direction after coupling the free leaf spring ends.

As the hinge-type coupling of the proximal free leaf spring ends is releasable, the instrument may be basically moved into a cleaning or sterilizing position by releasing the coupling/connection and thus taking the leaf springs/spring portions out of operation.

In accordance with the invention, the coupling of the two leaf spring ends basically comprises at least one hinge pin at one leaf spring end and at least one receiving eyelet on the other leaf spring end. The at least one eyelet has an inner diameter preferably with a small oversize compared to the at least one hinge pin for obtaining a swivel guide of the hinge pin in the eyelet that is substantially free from play. In this way, the leaf spring coupling may (indirectly) guide the resiliently flexible movements of the two leaf springs and thus also the pivoting of the two handles and in this way may counteract tilting of the handles.

For mounting the hinge-type leaf spring coupling this at least one eyelet includes a continuous longitudinal slit having a slit width that allows inserting the at least one hinge pin. The longitudinal slit is preferably placed at an angular position unlike the most proximal angular position of the eyelet, which prevents the hinge pin from being forced out of the at least one eyelet during surgical actuation of the instrument when also forces in the proximal direction are acting on the at least one hinge pin.

Due to the at least one eyelet having a longitudinal slit, it is comparatively simple to connect the proximal spring ends after conditioning/cleaning/sterilizing and also to uncouple them again, as the hinge pin need not be removed from and, resp., inserted into the eyelet in its longitudinal direction, but by appropriately deforming at least one of the leaf springs (which causes one of the leaf springs to be somewhat lengthened or shortened vis-à-vis the other one) the at least one hinge pin slides quasi on its own out of/into the longitudinal slit. That is to say that coupling/uncoupling is no longer effectuated by sensitive manipulation of the at least one hinge pin (almost impossible when wearing gloves) but by simple pressing/pulling at least one of the leaf springs.

In other words, the two opposite leaf springs are curved at least in the mounted/hinge-coupled state without any additional actuation (initial state) and preferably preformed in curved shape in the uncoupled state. The position of the axial slit is chosen depending on the curved shape (resulting at least in the initial state) of the two leaf springs so that, by pressing at least the one leaf spring including the bearing pin preferably at a predefined/marked location toward the opposite other leaf spring having a slotted bearing eye, the bearing eye is rotated by occurring bending of the pertinent one leaf spring (including the bearing eye) until the bearing pin slides through the axial slit out of the bearing eye. This is basically possible only when, according to the invention, the axial slit is provided on the side (hereinafter referred to as inner side) of the one leaf spring facing the other leaf spring (including the bearing pin).

In other words, the position of the axial slit is chosen so that the leaf springs can be uncoupled by curving the leaf spring including the bearing pin by pressing, preferably at a predefined/marked location in the direction of the opposite other leaf spring having a slotted bearing eye, (i.e. the radius of the curved shape of the leaf spring including the bearing pin is reduced) so that the force transmitted by the bearing pin to the bearing eye also curves the leaf spring including the slotted bearing eye (i.e. also the radius of the curved shape of the leaf spring including the slotted bearing eye is diminished), and when exceeding a threshold the force transmitted from the bearing pin to the bearing eye causes torsion of the leaf spring having a slotted bearing eye and thus twisting of the slotted bearing eye so that the bearing pin slides through the axial slit out of the bearing eye. This is basically possible only when, according to the invention, the axial slit is provided on the inner side of the leaf spring including a slotted bearing eye.

Preferably the position of the axial slit according to the invention is substantially distally opposed to the most proximal angular position of the bearing eye.

By the fact that the bearing pin is rotatably supported in the bearing eye the two grip portions including the respective curved leaf springs can be moved out of the starting position toward each other so that the curved shape of each of the leaf springs is retained and thus a resetting force is brought about which increases linearly or, resp., substantially linearly, with the grip portions moving toward each other and, resp., with the reduction of the angle between the two grip portions. A torsionally fixed support of the bearing pin within the bearing eye would result in the fact that, starting from their curved shape, the leaf springs are brought into an S shape (double curved shape having a turning point), when the two grip portions are moved toward each other out of the starting position. In this case, the resetting force is increased non-linearly with the reduction of the angle between the two grip portions.

Basically surgical handheld instruments can be structurally differentiated between forceps and scissors mechanism. In the case of forceps mechanisms the instrument levers (each consisting of a branch and a handle) extend substantially in parallel to each other, whereas in the case of scissors mechanisms the instrument levers intersect and are hinged to each other at the intersection point. The generic surgical handheld instrument for grasping, clamping, pinching or cutting an object or a patient's tissue follows the aforementioned scissors mechanism and accordingly comprises:

two elongate (intersecting and hinged to each other) instrument/lever elements each having a grip portion and a head or branch portion, a lever joint (hinge) connecting the two lever elements between their grip portion and their branch portion in a rotatable/hinge-like manner, wherein a spring portion (leaf spring) is connected to each of the two grip portions at the proximal ends thereof for mechanically connecting or coupling the two grip portions so that the two lever elements are retained in an open instrument position (in the starting or home position).

The hinged construction provided for this purpose at the proximal leaf spring ends includes at least two hinge elements, i.e. at least one hinge pin fixedly (preferably integrally) connected to the one spring portion at the proximal end thereof and an eyelet or bearing eye fixedly (preferably integrally) connected to the other spring portion at the proximal end thereof, wherein the eyelet or the bearing eye is configured in an open/slotted design such that the two hinge elements can be brought into and out of swivel coupling via the longitudinal slit without any further mounting measures, i.e. without any retrofitting, and wherein the longitudinal or axial slit is preferably arranged on the inner side of the pertinent leaf spring (according to the afore-mentioned definition).

The further development according to the invention of the generic surgical handheld instrument consists in configuring the hinge pin as a retaining pin that is fixedly connected at its two ends to the one spring portion at a free forked end of the one spring portion (closed design) and an eyelet/a roller at a free proximal end of the other spring portion, wherein the roller includes the (longitudinal) slit (open design) for radially inserting the hinge pin into the roller so that the roller encloses the retaining pin (partly/at least over three quarters of a circle).

Preferred embodiments of the surgical handheld instrument include, as an individually and independently claimable feature or combination of features, the fact that

- the slit in the roller extends diagonally with respect to the longitudinal roller axis so that upon inserting the hinge pin into the roller at least one spring portion has to be (additionally) elastically twisted;
- the slit in the roller extends substantially in parallel to the longitudinal roller axis and opens toward the branch portions;
- the spring portions have to be biased for coupling so that the retaining pin is retained in the roller and have to be displaced against the biasing force (in the longitudinal direction of the instrument toward the branch portions) (while bending at least one spring portion) so as to release the swivel coupling (connection) of the spring portions;
- the at least one hinge pin is configured to be out of the round in cross-section having at least one flattened portion, whereas the slit width is chosen to be so narrow that the hinge pin can be guided through the slit only alongside (within the area) of its at least one flattened portion,
- the roller can be spread in a resiliently elastic manner so as to widen the slit width for passing through the at least one hinge pin,
- at least one of the two leaf springs (spring portions) includes a marked actuating point in a central portion of the leaf spring in the area of which a manual pressure can be applied to the leaf spring so as to bend the latter in a predefined manner such that by the bending of the one leaf spring brought about according to the placing of the actuating point the at least one hinge pin is rotated relative to the eyelet until, due to the involved shortening of the one leaf spring vis-à-vis the other one, said hinge pin quasi automatically slides through the longitudinal slit out of the eyelet,
- each of the grip portions has a pitch circle type cross-section smaller than a semi-circle, has cavities at the respective sides facing each other in which interacting components of a circulation barrier are at least partly accommodated and, when the circulation barrier is locked, defines a gap or clearance therebetween the gap width of which forms a full circle having a substantially constant radius in interaction with the two pitch circles.

The surgical handheld instrument according to the invention offers the following advantages:

- It meets the requirement of the users requesting an easily manageable, elegant and releasable connection for spring ends on surgical instruments.
- In the hinged joint according to the invention at the proximal end of the spring portions the swivel coupling/connection has little/almost no play, as the hinge pin is inserted into the bearing eye radially via the longitudinal slit at the bearing eye. Therefore the risk of surgical gloves getting clamped during handling is low.
- The handling of the surgical handheld instrument is simple as no separate hinge elements such as pivot pins need to be inserted, but all hinge elements are fixedly connected to the spring portions.
- The solution presents itself in high optical quality.
- The effort required to manipulate the at least one spring for connecting the spring ends is low so that also the risk of bending and, resp., damaging the spring elements is low.

BRIEF DESCRIPTION OF THE DRAWING FIGURES

Further features and advantages of the invention will be evident from the following description in which the attached Figures will be referred to.

Figure 4:
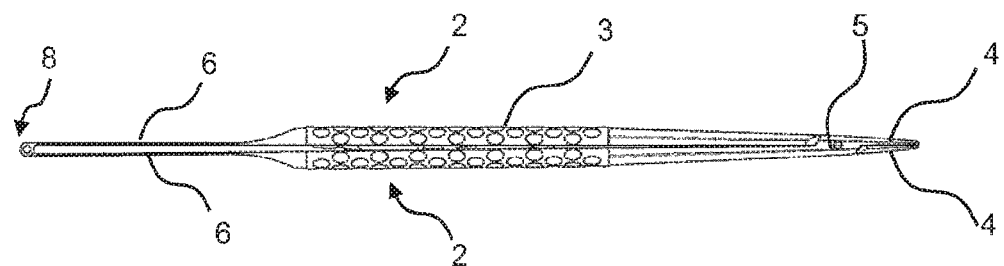
Figure 5:
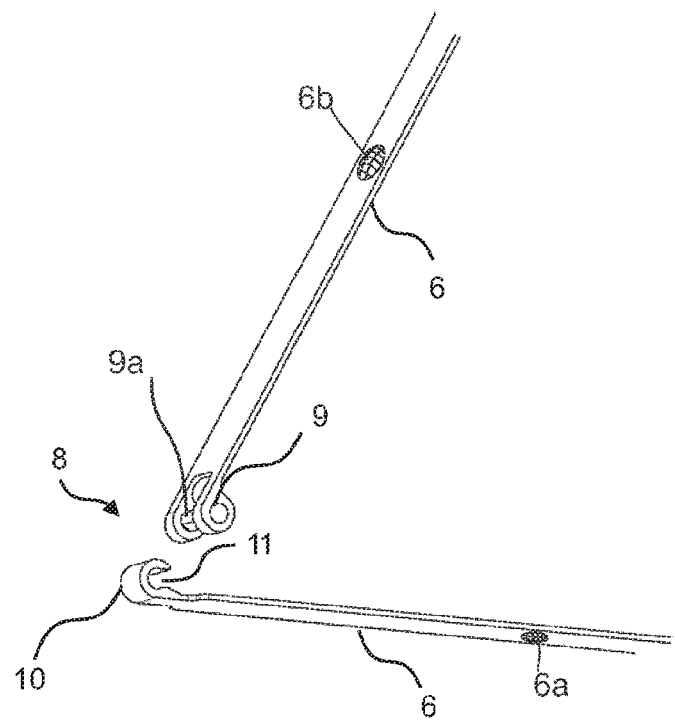
Figure 8:
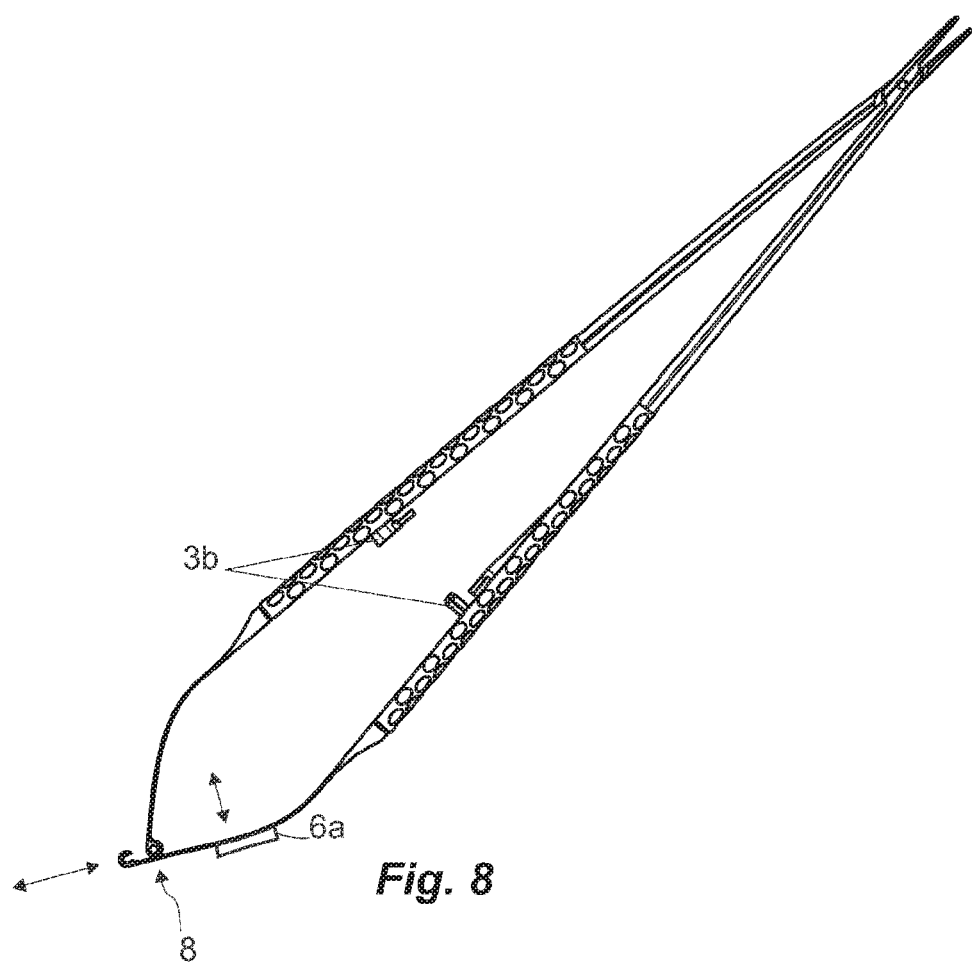
Figure 9:
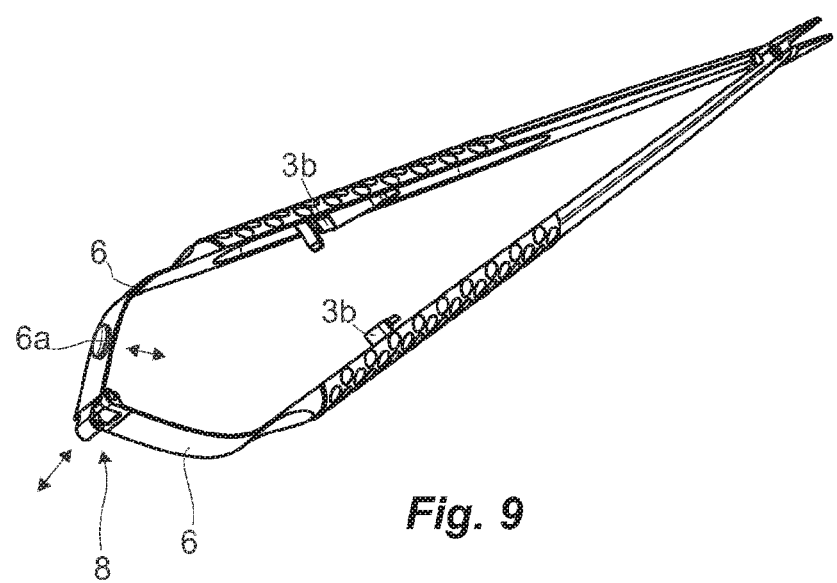

FIG. 1 shows a first embodiment of the (micro) surgical handheld instrument according to the invention in a perspective view in the opened state including leaf spring portions which are not yet pre-bent (semi-finished parts), FIG. 2 shows the first embodiment from a different perspective, FIG. 3 shows the proximal hinge according to the invention of the leaf spring portions/spring elements in accordance with FIG. 1 in an enlarged view as well as in the coupled/hooked state, FIG. 4 shows the handheld instrument according to the invention in accordance with FIG. 1 in a side view with a coupled proximal hinge and in the closed/actuated state, FIG. 5 shows the proximal hinge of the spring elements according to the invention in accordance with FIG. 1 in an enlarged representation as well as in an unhooked state (leaf springs are not yet plastically pre-bent in this case), FIG. 6 shows another embodiment of the proximal hinge according to the invention including a longitudinal slit inclined relative to the eyelet axis as well as including the two complete lever elements in the unfolded state (released distal hinge) in a perspective representation, FIG. 7 shows the embodiment according to FIG. 6 in a closed/actuated state, FIG. 8 shows in a perspective view the surgical instrument according to the invention in accordance with FIG. 1, i.e. in accordance with the first preferred embodiment of the present invention (however in contrast to FIGS. 1 to 9) in the finished state in which the two leaf spring elements are (plastically) pre-formed in curved shape relative to each other, with the proximal hinge being unhooked, however, and FIG. 9 shows a side view of the surgical instrument according to the invention in the finished state in accordance with FIG. 8 in which the proximal hinge is unhooked.

The Figures are not true to scale. Equal or equally acting elements are provided with the same reference numerals for all embodiments unless described to the contrary.

DETAILED DESCRIPTION

The coupling mechanism according to the invention (also referred to as closure mechanism) for resiliently coupling the actuating levers/instrument handles of a (micro) surgical handheld instrument preferably of the tongs or scissors design so that the jaw orifice formed by its branch portion is opened in a resiliently elastic manner shall be explained hereinafter by way of FIGS. 1 to 9.

In FIG. 1 a surgical handheld instrument 1 of the tongs/scissors design is illustrated having two lever elements 2 which are rotatably/pivotally interconnected via a joint/distal hinge 5. Each of the lever elements 2 includes a proximal grip portion (instrument handles) 3 and a distal branch or jaw portion 4 (jaw part). The joint/distal hinge 5 is provided between the grip portion 3 and the jaw portion 4 so that upon actuating (moving toward each other) the (integral) grip portions 3 of the lever elements 2 about the distal hinge 5 a tongs- or scissors-type closing movement of the distal jaw portions 4 is resulting. Said tongs-scissors mechanism is sufficiently known from the state of the art so that a detailed functional description will be dispensed with at this point.

In order to offer the option of retaining the lever elements 2 in an (opened and held apart) position in which no clamping force is exerted by the jaw portion 4 the two grip portions 3 are extended at the free ends thereof by a respective (leaf) spring 6 in the proximal direction. Each spring 6 preferably is a metal leaf, especially made of spring steel, which can be bent relatively easily and resiliently to a sufficient degree and can be twisted—viewed in the direction of the lever element 2—. Each metal sheet 6 extends substantially co-axially to the respective lever-type grip portion 3 and is fixedly connected or connectable thereto. For example, each metal leaf 6 is end-to-end soldered, welded, screwed or even integrally formed of one material with the pertinent grip portion.

It is pointed out in this context that the two leaf spring portions 6 according to FIG. 1 as well as according to the further FIGS. 2 to 7 are shown to be initially straight, hence are still in the semi-finished state. In FIGS. 8 and 9 the two leaf spring portions 6 are curved, on the other hand, i.e. are plastically preformed in curved shape. This constitutes the finished state of the leaf springs 6 in which the leaf springs 6 exert a biasing force counteracting the manual actuation on the grip portions 3 which forces/maintains the instrument into/in the open position.

The surgical handheld instrument 1 according to FIG. 1 is shown in a different perspective in FIG. 2.

From FIGS. 1 and 2 the difference in material thickness between the grip portion 3 and the spring portion 6 and thus an impression of the elastic flexibility of the spring portion 6 is evident vis-à-vis the (rigid) grip portion 3. Accordingly, the spring portions 6 are in the form of leaf springs and are thus elastically bendable in one direction (on one plane), whereas in a plane normal thereto the spring portions are rigid. Hence the spring elements 6 per se may basically adopt a guiding function for a pivoting movement about an axis normal to the bending plane.

The spring portions 6 are connected to the respective grip portion 3 at a distal end, as already described in the foregoing, with the other proximal end thereof being initially free. According to the invention, at said free proximal end 7 of the spring portions 6 a hinge joint 8 is provided which consists of two components interacting for the connection of the two lever elements 2 and, respectively, of the spring portions 6. The components of the hinged joint 8 will be described hereinafter by way of FIG. 3.

FIG. 3 illustrates the end side of the two spring portions 6 at each of the proximal free ends of which a component of the hinged joint 8 according to the invention is arranged. The upper one spring portion 6 according to FIG. 3 terminates in a holder including a hinge pin 9. Concretely speaking, at its proximal forked end the one spring portion 6 forms two opposite bearing blocks between which a hinge pin 9 is tightly inserted transversely to the longitudinal extension of the one spring portion 6 and transversely to the bending plane of the spring portion 6.

The other (according to FIG. 3 lower) spring portion 6 accordingly terminates in a bearing eye (eyelet) 10 which includes a longitudinal slit 11 extending in parallel to the bearing eye axis in the present example. Concretely speaking, the other spring portion 6 is bent at its proximal end to form a roller 10 which is not closed, however, but defines a gap or slit 11 radially opening in the direction of the branch portion, i.e. being generally located at an angular position unlike the most proximally located angular position of the roller 10.

Via the (longitudinal) slit 11 the hinge pin 9 is radially inserted into the roller 10 while bending the one spring portion 6 so that the roller 10 encloses the hinge pin 9 (at least three quarters of a circle thereof) and, apart from a rotating movement, any movement between the two spring portions 6 in the radial or axial direction of the roller 10 is rendered impossible. Equally, the hinge pin 9 may be removed from the roller 10 again without any separate components having to be removed from the hinge joint and to be stored. Consequently, handling of the handheld instrument is very simple.

FIG. 4 illustrates the tongs instrument according to the invention in a side view in the closed/actuated state in which the distal (scissors/tongs) hinge is mounted. Out of this closed state the tongs instrument then is opened again by the spring force of the two coupled spring portions 6 while releasing the grip portions 3.

For a more detailed explanation, the hinged joint 8 is shown in an unhooked state in FIG. 5. As is evident, the spring portion 6 is moved with the roller 10 toward its slit 11 and, respectively, the spring portion 6 is radially pushed into the slit 11 with the hinge pin 9. The slit 11 in this embodiment is somewhat narrower than the diameter of the hinge pin 9 so that it has to be pressed over the hinge pin 9 at the proximal end of the other spring portion 6 with a certain effort. This bottleneck offers the advantage that an inadvertent release of the hinged joint 8 is excluded during practical operation. There is any number of alternatives in this respect, however.

A preferred alternative provides adding a flattened portion 9a to the periphery of the hinge pin 9 (as is indicated in FIG. 5) or designing the pin cross-section to be out of the round, e.g. according to an ellipse. In this case, the slit width is selected so that the pin can only be inserted into the roller 10 in the area of its flattened portion 9a. The angular position of the flattened portion 9a in turn is selected so that does not comply with the slit 11 over the usual swivel angle range of the instrument. In this way the pin 9 can be prevented from slipping out during use of the surgical instrument.

As may be further inferred from FIG. 5, markings (push-buttons) 6a, 6b are provided on the flat sides of the leaf spring portions 6 facing away from each other in a central longitudinal portion of each of the leaf springs 6. Said markings 6a, 6b may be produced by color prints or surface modifications such as roughening, ribs etc., where appropriate, and define respective pressure points. It is referred to the fact that the respective marking of only one of the two leaf springs 6, preferably that including the roller 10, is sufficient for the function described in the following.

The invention is not restricted to the representation in FIGS. 1 to 5. Especially different forms are imaginable with respect to the configuration of the roller 10 including the slit 11. Such alternative is shown in FIGS. 6 and 7.

The main components of the surgical handheld instrument according to the invention in FIGS. 6 and 7 have been explained already in the foregoing Figures. In the embodiment of the handheld instrument according to FIG. 6 the roller 10 is not opened in the direction of the branch portion 4 by the axial slit 11, unlike the previous embodiments, but instead is opened in slit shape in the opposite direction.

Furthermore, the slit 11 is (slightly) inclined or extends diagonally vis-à-vis the spring portion 6 and, resp., with respect to the longitudinal roller axis. This means that the spring portion 6 including the roller 10 and/or the spring portion 6 including the hinge pin 8 have to be slightly twisted (about the longitudinal axis of the lever elements 2) so as to insert the hinge pin 9 into the slit 11 and thus assemble the hinged joint 8. When subsequently the spring portion 6 is released to untwist again, the hinge pin 9 slips through the slit 11 into the roller 10. In this context it is pointed out that the hinge pin 9 in this case does not require any flattened portion and the slit width may correspond to the pin diameter.

The handheld instrument according to FIG. 6 in the closed state is illustrated in FIG. 7. Accordingly, another feature of the handheld instrument according to the invention is shown which is applicable to all embodiments, by the way:

As illustrated, the grip portions 3 have a shell design in the present case, each grip portion 3 in cross-section forming a pitch circle that is smaller than a semi-circle. The shell shape serves for receiving the components of a circulation barrier 3b known per se, i.e. especially a cam component at the one grip portion and an interacting link component at the other grip portion. Circulation barriers of this type belong to the generally known prior art and therefore need not be described in detail here.

In accordance with the invention it is provided now to adjust the pitch circle of each grip portion 3 to the used circulation barrier of a known design such that in the closed and locked state of the instrument according to FIG. 9 a full circle is formed in the area of the grip portions 3 which is formed by the pitch circles of the two grip portions 3 as well as a clearance 3a between the two grip handles 3 which is functionally required for actuation of the currently used circulation barrier 3b. Such full circle shape having a substantially constant radius has turned out to be advantageous for handling the instrument, as the closed and locked instrument can be rotated in any way safely and evenly about the longitudinal axis thereof without the instrument tilting between the fingers. Hence it is also ensured that the instrument jaw part 4 can be safely guided.

In FIGS. 8 and 9 the instrument according to the invention is illustrated in the finished and mounted state, wherein also the two components of the circulation barrier 3b are indicated.

Accordingly, the two spring portions 6 are plastically deformed into a curved shape so as to force the grip portions 3 apart. When in this state in which the proximal hinge 8 is coupled the two grip portions 3 are pressed against each other, the two leaf spring elements 6 experience elastic bending/stretching while swiveling against each other within the proximal hinge 8. Upon release of the grip portions 3 the two leaf spring elements 6 force the instrument back into its open position. When the manual actuation is carried out over a particular pivot point, the circulation barrier 3b locks in place and thus retains the instrument in its closing position.

In order to uncouple the proximal hinge 8 with a non-inclined slit 11 according to the first preferred embodiment of the present invention at least the one leaf spring element with the end-side roller 10 is indented sideward in the area of the marking 6a. In this way said spring element bends, thus causing the roller 10 to start rotating with respect to the hinge pin 9. At the same time, said one leaf spring element stretches and thus exerts a pressure on the roller 10 in the proximal direction.

At a defined actuating distance the longitudinal slit 11 comes to lie within the area of the flattened portion 9a of the hinge pin 9 and the roller 10 is displaced in the proximal direction over the hinge pin 9. Thus the proximal hinge 8 is uncoupled.

Summing up, the invention excels as to the following aspects vis-à-vis the state of the art:

In the present invention the connection/swivel coupling of the two spring portions 6 is realized by such hinge joint 8 which can do without projecting tabs for the connection of the spring ends.

In an embodiment the bearing eye/roller 10 of the hinge 8 is diagonally slotted so that the pin 9 of the hinge 8 can be withdrawn/inserted by slightly rotating/twisting at least the one spring end. In another embodiment the bearing eye/roller 10 of the hinge is slotted so that the pin 9 has to be guided toward the branch portion along the leaf spring for release, with the one spring portion 6 being elastically curved. The pin 9 is retained in the roller 10 of the hinge 8 in its rotatable functional position via the spring tension of both spring portions 6 and the positive closure (hinge pin 9 within the roller 10). As another embodiment, the swivel coupling/connection may be a snap/click connection.

Summing up, the invention relates to a surgical handheld instrument 1 for grasping an object comprising: two lever elements 2 each including a grip portion 3 and a jaw/branch portion 4, a lever joint 5 which connects the two lever elements rotatably to each other between their grip portion and their branch portion, wherein each of the two grip portions is adjoined by a respective spring portion 6 for connecting the two grip portions such that the two lever elements 2 are held resiliently in an open position. To create an easily manageable and elegant releasable connection for spring ends on surgical instruments the handheld instrument comprises a hinge pin 9 fixedly connected thereto at a free end 7 of one spring portion and a bearing eye 10 fixedly connected thereto at a free end 7 of the other spring portion, wherein the bearing eye has a longitudinal slit 11 for radial insertion of the hinge pin 9 into the bearing eye 10.

What is claimed:

1. A surgical handheld instrument comprising:
a first lever element and a second lever element hinged to the first lever element by a lever element hinge, each lever element including a grip portion on a first side of the lever element hinge and a jaw portion on a second side of the lever element hinge,
a first leaf spring and a second leaf spring which are proximally connected to each of the grip portions as a first spring portion and a second spring portion, respectively, the first spring portion and the second spring portion extending each of the grip portions, the first leaf spring and the second leaf spring each having a proximal free end, the proximal free end of the first leaf spring being coupled to the proximal free end of the second leaf spring by a hinged joint, the hinged joint including a hinge pin at the proximal free end of the first leaf spring and at least one bearing eye at the proximal free end of the second leaf spring,
wherein the at least one bearing eye comprises an eye-hole having a longitudinal axis extending therethrough,
wherein the at least one bearing eye also comprises a continuous longitudinal slit extending diagonally through the at least one bearing eye relative to the longitudinal axis of the eye-hole,
wherein, when the first lever element and the second lever element are hinged together by the lever element hinge, at least one spring portion must be twisted so as to align a longitudinal axis of the hinge pin with the slit to allow for radial insertion of the hinge pin into the at least one bearing eye.

2. The surgical handheld instrument according to claim 1, wherein the slit comprises a slit width that is smaller than a maximum diameter of the hinge pin.

3. The surgical handheld instrument according to claim 1, wherein the at least one bearing eye can be resiliently widened.

4. The surgical handheld instrument according to claim 1, wherein the grip portions:
   each have a circular cross-section smaller than a semicircle;
   on sides facing each other, include cavities in which interacting components of a circulation barrier are at least partially accommodated; and
   when the circulation barrier is locked in place, define a gap or clearance between the grip portions, such that the cross-sections of the grip portions occupy a shape of a circle having a radius that coincides with a radius of each of the circular cross-sections of the grip portions.

5. The surgical handheld instrument according to claim 1, wherein the first spring portion and the second spring portion are biased against each other in a mounted state of the hinged joint so that the hinge pin is retained in the at least one bearing eye by a biasing force and has to be displaced against the biasing force out of the slit so as to release the hinged joint.

6. The surgical handheld instrument according to claim 1, wherein in a mounted state of the hinged joint, the hinge pin is rotatably connected to the at least one bearing eye so that a resetting force resulting from compression of the grip portions at least substantially linearly increases upon reduction of an angle between the grip portions.

7. The surgical handheld instrument according to claim 1, wherein the slit formed in the at least one bearing eye opens in a direction opposite a direction of the second leaf spring.

8. The surgical handheld instrument according to claim 1, wherein the slit comprises a width and the hinge pin comprises a diameter equal to the width of the slit.

9. The surgical handheld instrument according to claim 1, wherein the first grip portion and the second grip portion each have a first thickness, and the first spring portion and the second spring portion each have a second thickness less than the first thickness.

10. A surgical handheld instrument comprising:
    a first lever element and a second lever element hinged to the first lever element by a lever element hinge, each lever element including a grip portion on a first side of the lever element hinge and a jaw portion on a second side of the lever element hinge,
    a first leaf spring and a second leaf spring which are proximally connected to each of the grip portions as a first spring portion and a second spring portion, respectively, the first spring portion and the second spring portion extending each of the grip portions, the first leaf spring and the second leaf spring each having a proximal free end, the proximal free end of the first leaf spring being coupled to the proximal free end of the second leaf spring by a hinged joint, the hinged joint including a hinge pin at the proximal free end of the first leaf spring and at least one bearing eye at the proximal free end of the second leaf spring,
    wherein the at least one bearing eye comprises an eyehole having a longitudinal axis extending therethrough, wherein the at least one bearing eye also comprises a continuous longitudinal slit extending diagonally through the at least one bearing eye relative to the longitudinal axis of the eye-hole,
    wherein, when the first lever element and the second lever element are hinged together by the lever element hinge, the hinge pin can only be radially inserted into the at least one bearing eye once a longitudinal axis of the hinge pin and the slit are caused to become aligned from a misaligned orientation by twisting at least one spring portion.

\* \* \* \* \*